United States Patent
Lawhorn

(10) Patent No.: US 10,799,623 B2
(45) Date of Patent: *Oct. 13, 2020

(54) SYSTEM AND METHOD FOR DISTINGUISHING LEAKS FORM A DISENGAGED CANISTER CONDITION IN A REDUCED PRESSURE TREATMENT SYSTEM

(71) Applicant: KCI Licensing, Inc., San Antonio, TX (US)

(72) Inventor: Thomas Paul Lawhorn, Denham Springs, LA (US)

(73) Assignee: KCI Licensing, Inc., San Antonio, TX (US)

( * ) Notice: Subject to any disclaimer, the term of this patent is extended or adjusted under 35 U.S.C. 154(b) by 393 days.

This patent is subject to a terminal disclaimer.

(21) Appl. No.: 15/870,510

(22) Filed: Jan. 12, 2018

(65) Prior Publication Data

US 2018/0137746 A1 May 17, 2018

Related U.S. Application Data

(60) Continuation of application No. 14/326,260, filed on Jul. 8, 2014, now Pat. No. 9,905,123, which is a
(Continued)

(51) Int. Cl.
*A61M 1/00* (2006.01)
*G08B 19/00* (2006.01)
*G08B 31/00* (2006.01)

(52) U.S. Cl.
CPC ........ *A61M 1/0031* (2013.01); *A61M 1/0088* (2013.01); *G08B 19/00* (2013.01);
(Continued)

(58) Field of Classification Search
CPC .................. A61M 1/0031; A61M 1/0088
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Susan S Su

(57) ABSTRACT

A method of distinguishing leak detection and canister disengagement in a reduced pressure treatment system includes monitoring an actual power level and a source pressure of a reduced pressure pump. The actual power level is compared to a target power level, and the source pressure is compared to a first alarm pressure and a second alarm pressure. A leak alarm is indicated when the actual power level is greater than the target power level and the source pressure is greater than the first alarm pressure. A canister disengaged alarm is indicated when the actual power level is greater than the target power level and the source pressure is less than the second alarm pressure.

22 Claims, 2 Drawing Sheets

Related U.S. Application Data division of application No. 12/070,891, filed on Feb. 20, 2008, now Pat. No. 7,927,319.

(60) Provisional application No. 60/902,267, filed on Feb. 20, 2007.

(52) U.S. Cl.
CPC ......... *G08B 31/00* (2013.01); *A61M 2205/14* (2013.01); *A61M 2205/15* (2013.01); *A61M 2205/18* (2013.01)

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower Guiles, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,015 A | 7/1986 | Evans et al. |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,059,171 A | 10/1991 | Bridge et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,142,982 A | 11/2000 | Hunt et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0173253 A1 | 8/2006 | Ganapathy et al. |
| 2007/0016152 A1 | 1/2007 | Karpowicz et al. |
| 2007/0032763 A1 | 2/2007 | Vogel |
| 2008/0071214 A1 | 3/2008 | Locke et al. |
| 2010/0100075 A1 | 4/2010 | Weston et al. |
| 2010/0286489 A1 | 11/2010 | Hartwell |
| 2014/0163491 A1 | 6/2014 | Schuessler et al. |
| 2015/0080788 A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |

(56) References Cited

FOREIGN PATENT DOCUMENTS

| | | |
|---|---|---|
| EP | 0117632 A2 | 9/1984 |
| EP | 0161865 A2 | 11/1985 |
| EP | 0358302 A2 | 3/1990 |
| EP | 1018967 A1 | 7/2000 |
| FR | 2766083 A1 | 1/1999 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2342584 A | 4/2000 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 9903518 A1 | 1/1999 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp: 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Pěska, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax, " Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II" ).

(56) References Cited

OTHER PUBLICATIONS

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

Indian Examination Report for corresponding Application No. 5928/DELNP/2009, dated Jan. 12, 2018.

European Examination report for corresponding Application No. 161724778, dated Aug. 10, 2018.

SYSTEM AND METHOD FOR DISTINGUISHING LEAKS FORM A DISENGAGED CANISTER CONDITION IN A REDUCED PRESSURE TREATMENT SYSTEM

CROSS-REFERENCE TO RELATED APPLICATIONS

This application is a continuation of U.S. patent Ser. No. 14/326,260, filed Jul. 8, 2014, which is a continuation of U.S. patent application Ser. No. 13/070,340, filed Mar. 23, 2011, which is a divisional of U.S. patent application Ser. No. 12/070,891, filed Feb. 20, 2008, now U.S. Pat. No. 7,927,319 which claims the benefit of U.S. Provisional Application No. 60/902,267, filed Feb. 20, 2007, which is hereby incorporated by reference.

BACKGROUND

1. Field of the Invention

The present invention relates generally to tissue treatment systems and in particular to a reduced pressure treatment system having a system for distinguishing between a leak condition and a disengaged canister condition.

2. Description of Related Art

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

One problem with current reduced pressure systems is the interruption of reduced pressure to the tissue site when a leak develops in the system or a component of the system, such as a fluid collection canister, becomes disengaged. Previous reduced pressure systems used a flow sensor to determine the amount of air flow moving through the reduced pressure system. Upon detecting a "high" flow rate, an alarm condition indicating "Canister Not Engaged" was typically activated. If a slightly lower flow rate was detected, it was assumed that a leak had developed, and an alarm condition indicating such was activated. Using a flow sensor to detect these conditions has certain drawbacks. The addition of flow sensors to the reduced pressure system requires additional hardware and the associated software required to receive and process data from the flow sensors. The flow sensors also may exhibit decreased accuracy due to certain environmental conditions. For example, when the flow rate sensor determines flow by measuring a pressure drop across an orifice, temperature conditions may dramatically affect the hardware sensing the pressure drop, thereby presenting errors in the final flow rate determination.

SUMMARY

The problems presented by existing detection systems are solved by the systems and methods of the illustrative embodiments described herein. In one embodiment, a method of distinguishing leak detection and canister disengagement in a reduced pressure treatment system includes monitoring an actual power level and a source pressure of a reduced pressure pump. The actual power level is compared to a target power level, and the source pressure is compared to a first alarm pressure and a second alarm pressure. A leak alarm is indicated when the actual power level is greater than the target power level and the source pressure is greater than the first alarm pressure. A canister disengaged alarm is indicated when the actual power level is greater than the target power level and the source pressure is less than the second alarm pressure.

In another embodiment, a method of distinguishing leak detection and canister disengagement in a reduced pressure treatment system includes monitoring an actual power level and a target power level of a reduced pressure source. The actual power level is compared to the target power level using a processing unit. In response to the actual power level exceeding the target power level for a selected period of time, the processing unit communicates at least one of a leak alarm signal and a canister disengaged alarm signal to an alarm indicator, wherein the alarm indicator generates an alarm in response to receiving the at least one of the leak alarm signal and the canister disengaged alarm signal.

In still another embodiment, a method of distinguishing leak detection and canister disengagement in a reduced pressure treatment system includes monitoring an actual power level and a target power level of a reduced pressure source. The actual power level is compared to the target power level. A source pressure as determined by a sensor in communication with the reduced pressure source is further monitored. The source pressure is compared to a first and second alarm pressure. In response to the actual power level exceeding the target power level for a selected period of time and the source pressure being greater than the first alarm pressure, a leak alarm signal is communicated to an alarm indicator. If the alarm indicator receives the leak alarm signal, a first alarm is generated by the alarm indicator. In response to the actual power level exceeding the target power level for the selected period of time and the source pressure being less than the first alarm pressure, a canister disengaged signal is communicated to the alarm indicator. If the alarm indicator receives the canister disengaged signal, a second alarm is generated by the alarm indicator.

Other objects, features, and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the invention is defined only by the appended claims.

The term "reduced pressure" as used herein generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure of tissue at the tissue site. Although the terms "vacuum" and "negative pressure" may be used to describe the pressure applied to the tissue site, the actual pressure applied to the tissue site may be significantly less than the pressure normally associated with a complete vacuum. Reduced pressure may initially generate fluid flow in the tube in the area of the tissue site. As the hydrostatic pressure around the tissue site approaches the desired reduced pressure, the flow may subside, and the reduced pressure is then maintained. Unless otherwise indicated, values of pressure stated herein are gauge pressures. Similarly, references to increases in reduced pressure typically refer to a decrease in absolute pressure, while decreases in reduced pressure typically refer to an increase in absolute pressure.

The term "tissue site" as used herein refers to a wound or defect located on or within any tissue, including but not limited to, bone tissue, adipose tissue, muscle tissue, neural tissue, dermal tissue, vascular tissue, connective tissue, cartilage, tendons, or ligaments. The term "tissue site" may further refer to areas of any tissue that are not necessarily wounded or defective, but are instead areas in which it is desired to add or promote the growth of additional tissue. For example, reduced pressure tissue treatment may be used in certain tissue areas to grow additional tissue that may be harvested and transplanted to another tissue location.

Figure 1:
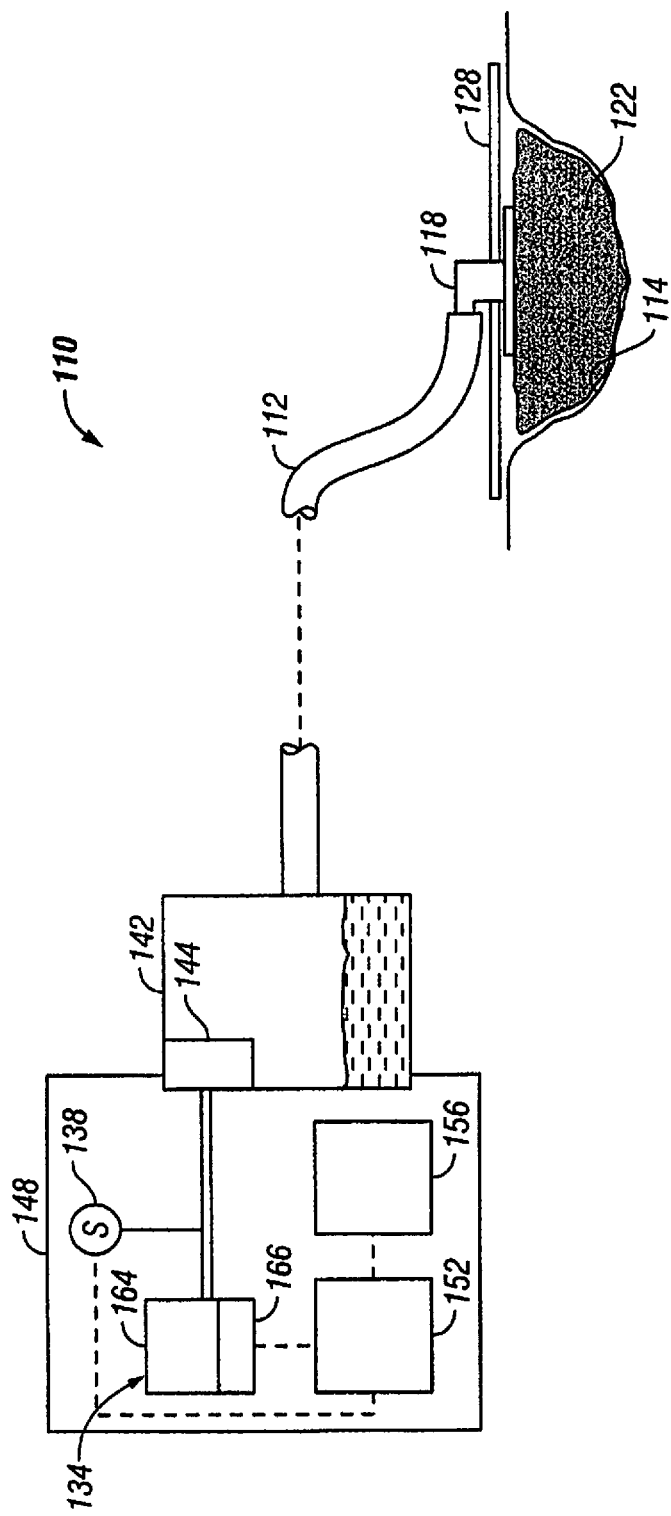
FIG. 1 illustrates a reduced pressure treatment system configured to indicate leak conditions and canister disengaged conditions according to an embodiment of the invention.

Referring to FIG. 1, a reduced pressure treatment system 110 according to an embodiment of the invention includes a conduit 112 in fluid communication with a tissue site 114 of a patient. The conduit 112 may fluidly communicate with the tissue site 114 through a tubing adapter 118 and a distribution manifold 122. The distribution manifold 122 may be any material, either bioabsorbable or non-bioabsorbable, that is capable of manifolding a reduced pressure to the tissue site 114. In one embodiment, the distribution manifold 122 may be an open-cell, reticulated polyurethane foam. A drape 128 may be placed over the distribution manifold 122 and sealed around a perimeter of the tissue site 114 to maintain reduced pressure at the tissue site 114.

The conduit 112 is fluidly connected to a reduced pressure source 134. A sensor 138 is disposed at or near the reduced pressure source 134 to determine a source pressure generated by the reduced pressure source 134. In one embodiment, the sensor 138 may be a pressure transducer. A canister 142 is fluidly connected between the reduced pressure source 134 and the tissue site 114 to collect exudate and other fluids drawn from the tissue site 114. The canister 142 may include a hydrophobic filter 144 positioned near an outlet of the canister 142 to prevent fluid from exiting the canister and contaminating the reduced pressure source 134.

In one implementation, the canister 142 may be detachably cooperative with a treatment unit 148 that includes the reduced pressure source 134.

The reduced pressure system 110 may further include a processing unit 152 that communicates with at least one of the reduced pressure source 134, the sensor 138, and an alarm indicator 156. The processing unit 152 may include one or more processors, logic, analog components, or any other electronics that enable signals including information, such as source pressure at a reduced pressure source, to be received. The processing unit 152 may process the information provided by the signals. For example, a source pressure signal may be received by the processing unit 152 and a leak alarm and/or canister disengaged alarm may be driven by the processing unit 152.

In one implementation, the reduced pressure source 134 may be a reduced pressure or vacuum pump 164 driven by a motor 166. The processing unit 152 may configured to receive signals from the motor 166 or components associated with the motor 166 to determine an actual power level that is being required to drive the vacuum pump 164. The processing unit 152 compares the actual power level to a target power level at which the reduced pressure source 134 is initially calibrated to run. When the actual power level exceeds the target power level for a selected period of time, either a leak condition or a canister disengagement condition exists within the reduced pressure system 110. In either of these conditions, the tissue site 114 experiences at least a partial interruption in the supply of reduced pressure. For example, if a leak occurs between the drape 128 and the perimeter of the tissue site 114, it becomes very difficult to maintain a reduced pressure at the tissue site 114. Similarly, if the canister 142 becomes disengaged from the treatment unit 148, the supply of reduced pressure is interrupted. In either of these conditions, additional power is required by the motor 166 and the pump 164 to attempt to maintain a particular level of reduced pressure at the tissue site 114.

To distinguish between a leak condition and a canister disengaged condition, the processing unit 152 monitors the source pressure determined by the sensor 138. When the canister 142 is disengaged, the source pressure is substantially lower than when the canister is engaged because the vacuum pump 164 is not required to maintain the negative pressure through the hydrophobic filter 144 of the canister 142. Thus, to determine a canister disengaged condition, the processing unit 152 compares the source pressure to a first alarm pressure. If the source pressure is below the first alarm pressure, the processing unit communicates a canister disengaged alarm signal to the alarm indicator 156. When the source pressure remains high, thus indicating that the canister 142 is engaged, then the condition is by default a leak condition. In one configuration, the source pressure may be compared by the processing unit 152 to a second alarm pressure, and when the source pressure exceeds the second alarm pressure, a leak condition is declared. When a leak condition is determined, the processing unit communicates a leak alarm signal to the alarm indicator. In one embodiment, the first and second alarm pressures are equal.

The alarm indicator 156 is capable of generating distinctive alarms in response to receiving leak alarm and canister disengaged alarm signals from the processing unit 152. The alarm indicator may be an audible indicator such as a speaker or a visual indicator such as LEDs or other lights, or alternatively an LCD or other display.

Figure 2:
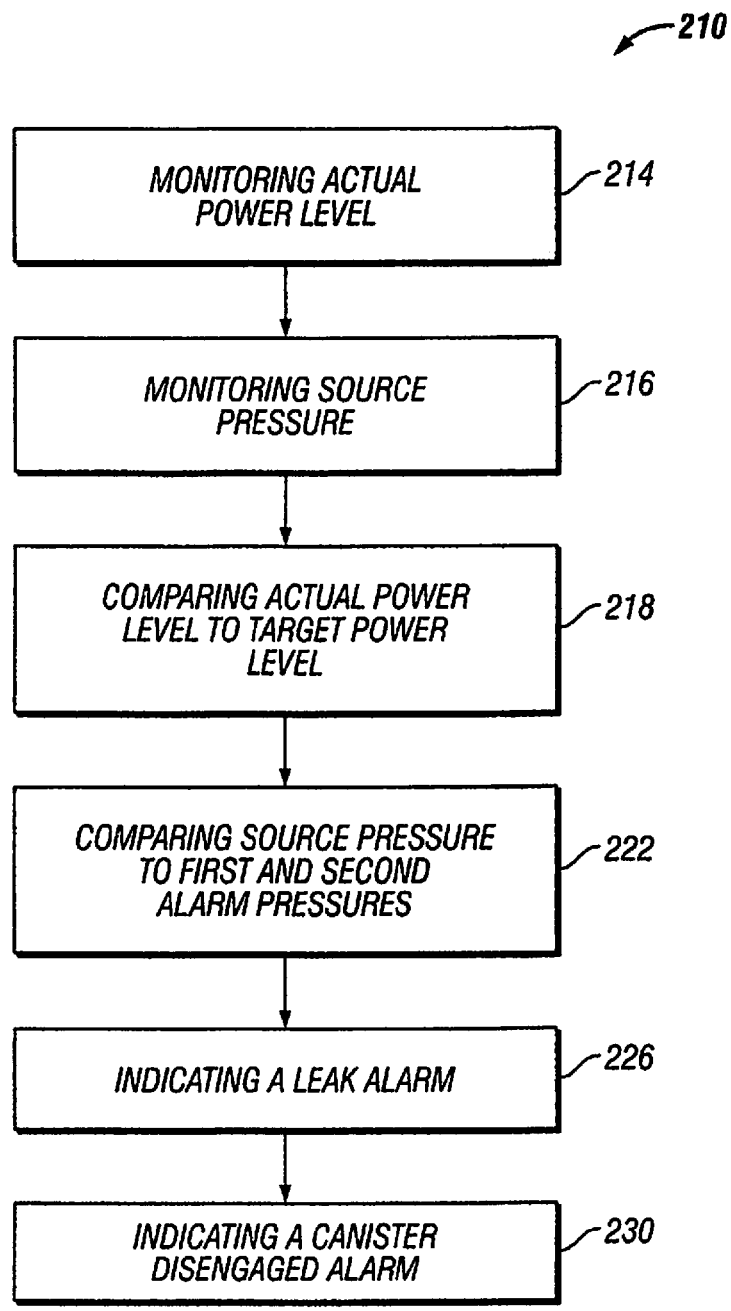
FIG. 2 depicts a method of distinguishing a leak condition from a canister disengagement condition according to an embodiment of the invention.

Referring to FIG. 2, an exemplary method 210 for distinguishing between a leak condition and a canister disengagement condition in a reduced pressure treatment system is provided. The method includes at step 214 monitoring an actual power level and, at step 216, monitoring a source pressure of a reduced pressure pump. At step 218, the actual power level is compared to a target power level, and at step 222, the source pressure is compared to a first alarm pressure and a second alarm pressure. At step 226, a leak alarm is indicated when the actual power level is greater than the target power level and the source pressure is greater than the first alarm pressure. A canister disengaged alarm is indicated at step 230 when the actual power level is greater than the target power level and the source pressure is less than the second alarm pressure.

It should be apparent from the foregoing that an invention having significant advantages has been provided. While the invention is shown in only a few of its forms, it is not just limited but is susceptible to various changes and modifications without departing from the spirit thereof.

I claim:

1. A reduced-pressure treatment apparatus comprising:
   a reduced-pressure source including a pump driven by a motor;
   a sensor configured to monitor a power level of the motor;
   a pressure sensor configured to measure a pressure generated by the pump; and
   a processing unit electrically coupled to the sensor and the pressure sensor, the processing unit configured to:
      read the power level of the motor required to drive the pump as a monitored power level,
      read the pressure of the pump from the pressure sensor as a measured pressure,
      compare the monitored power level to a target power level to determine that a leak condition or a canister-disengaged condition may exist, and
      compare the measured pressure to an alarm pressure to determine that one of the leak condition or the canister-disengaged condition exists as an identified condition; and
   an alarm indicator electrically coupled to the processing unit configured to provide an alarm signal indicating the identified condition.

2. The reduced-pressure treatment apparatus of claim 1, wherein the alarm indicator is configured to generate an alarm signal if the monitored power level is greater than the target power level.

3. The reduced-pressure treatment apparatus of claim 1, wherein the alarm indicator is configured to generate a leak alarm signal if the monitored power level is greater than the target power level and the measured pressure is greater than an alarm pressure.

4. The reduced-pressure treatment apparatus of claim 1, wherein the alarm pressure is a first alarm pressure and the alarm indicator is configured to generate a canister-disengaged alarm signal if the monitored power level is greater than the target power level and the measured pressure is less than a second alarm pressure.

5. The reduced-pressure treatment apparatus of claim 4, wherein the first alarm pressure and the second alarm pressure are the same.

6. The reduced-pressure treatment apparatus of claim 1, wherein the alarm indicator is configured to generate a leak alarm or a canister-disengaged alarm.

7. The reduced-pressure treatment apparatus of claim 1, wherein the alarm indicator is an audible alarm indicator.

8. The reduced-pressure treatment apparatus of claim 1, wherein the alarm indicator is a visual alarm indicator.

9. The reduced-pressure treatment apparatus of claim 1, wherein the motor is calibrated to operate at the target power level.

10. The reduced-pressure treatment apparatus of claim 1, further comprising:
    a canister;
    a hydrophobic filter; and
    a conduit configured to fluidly couple the reduced-pressure source to a tissue site via the canister and the hydrophobic filter.

11. A reduced-pressure treatment apparatus comprising:
    a sensor configured to monitor a power level of a motor;
    a pressure sensor configured to measure a pressure generated by a pump coupled to the motor; and
    a processing unit configured to:
       read the power level of the motor from the sensor as a monitored power level,
       read the pressure of the pump as a measured pressure,
       compare the monitored power level to a target power level to determine that a leak condition or a canister-disengaged condition may exist, and
       compare the measured pressure to an alarm pressure to determine that one of the leak condition or the canister-disengaged condition exists as an identified condition; and
    an alarm indicator configured to provide an alarm signal indicating the identified condition in response to determining the identified condition.

12. The reduced-pressure treatment apparatus of claim 11, wherein the motor is calibrated to operate at the target power level.

13. The reduced-pressure treatment apparatus of claim 11, wherein the processing unit is further configured to communicate the alarm signal to the alarm indicator if the monitored power level is greater than the target power level.

14. The reduced-pressure treatment apparatus of claim 11, wherein the processing unit is further configured to communicate a leak alarm signal to the alarm indicator if the monitored power level is greater than the target power level and the measured pressure is greater than the alarm pressure.

15. The reduced-pressure treatment apparatus of claim 11, wherein the alarm pressure is a first alarm pressure and the processing unit is further configured to communicate a canister-disengaged alarm signal to the alarm indicator if the monitored power level is greater than the target power level and the measured pressure is less than a second alarm pressure.

16. The reduced-pressure treatment apparatus of claim 15, wherein the first alarm pressure and the second alarm pressure are the same.

17. The reduced-pressure treatment apparatus of claim 11, wherein the alarm indicator is configured to indicate a leak alarm signal or a canister-disengaged alarm signal.

18. A method for determining a leak condition and a canister-disengaged condition, the method comprising:
    reading a power level of a motor configured to drive a pump in a reduced-pressure source as a monitored power level;
    reading a pressure of the pump as a measured pressure;
    comparing the monitored power level to a target power level;
    determining that a leak condition or a canister-disengaged condition may exist in response to comparing the monitored power level to the target power level;
    comparing the measured pressure to an alarm pressure;

determining one of the leak condition or the canister-disengaged condition exists as an identified condition in response to comparing the measured pressure to the alarm pressure; and indicating the identified condition with an alarm indicator.

19. The method of claim 18, wherein the method further comprises monitoring the power level of the motor over a selected period of time.

20. The method of claim 18, wherein the method further comprises communicating a leak alarm signal to the alarm indicator if the monitored power level is greater than the target power level and the measured pressure is greater than the alarm pressure.

21. The method of claim 18, wherein the alarm pressure is a first alarm pressure and the method further comprises communicating a canister-disengaged alarm signal to the alarm indicator if the monitored power level is greater than the target power level and the measured pressure is lower than a second alarm pressure.

22. The method of claim 21, wherein the first alarm pressure and the second alarm pressure are the same.

\* \* \* \* \*